United States Patent [19]

Sangokoya

[11] Patent Number: 5,565,397
[45] Date of Patent: * Oct. 15, 1996

[54] OLEFIN POLYMERIZATION CATALYST COMPRISING A METALLOCENE AND AN ANHYDROUS LITHIUM HALIDE-TREATED ALKYLALUMINOXANE

[75] Inventor: Samuel A. Sangokoya, Baton Rouge, La.

[73] Assignee: Albemarle Corporation, Richmond, Va.

[*] Notice: The term of this patent shall not extend beyond the expiration date of Pat. No. 5,157,137.

[21] Appl. No.: 440,037

[22] Filed: May 12, 1995

Related U.S. Application Data

[62] Division of Ser. No. 123,779, Sep. 20, 1993, abandoned.

[51] Int. Cl.$^6$ ...................................................... C08F 4/606

[52] U.S. Cl. ........................ 502/129; 502/117; 502/152; 502/154; 502/111; 526/124.1; 526/160

[58] Field of Search ..................................... 502/103, 129, 502/111, 117, 152, 154; 526/123.1, 124.1, 160

[56] References Cited

U.S. PATENT DOCUMENTS

| | | | |
|---|---|---|---|
| 5,099,050 | 3/1992 | Sangokoya | 556/179 |
| 5,117,020 | 5/1992 | Razavi | 556/43 |
| 5,157,137 | 10/1992 | Sangokoya | 556/179 |

*Primary Examiner*—Romulo H. Delmendo
*Attorney, Agent, or Firm*—Philip M. Pippenger

[57] ABSTRACT

Alkylaluminoxanes having improved catalytic activity such as when they are used in combination with metallocenes for the polymerization of alpha-olefins, are prepared by treating an organic solvent solution of an alkylaluminoxane, such as methylaluminoxane, with anhydrous lithium halide.

7 Claims, No Drawings

OLEFIN POLYMERIZATION CATALYST COMPRISING A METALLOCENE AND AN ANHYDROUS LITHIUM HALIDE-TREATED ALKYLALUMINOXANE

This application is a division of application Ser. No. 08/123,779, filed Sep. 20, 1993, now abandoned.

This invention relates generally to alkylaluminoxanes and more specifically to alkylaluminoxanes having both increased solubility in organic solvents and increased catalytic activity which are prepared by treating alkylaluminoxanes with anhydrous lithium halide salts.

My U.S. Pat. No. 5,157,137 relates to a process for forming clear, gel free solutions of alkylaluminoxanes by treating a solution of the alkylaluminoxane with an anhydrous salt and/or hydroxide of an alkali or alkaline earth metal. I now have found that alkylaluminoxanes treated with anhydrous lithium chloride, bromide or iodide have both improved organic solvent solubility and improved catalytic activity when used in olefin polymerization.

In accordance with this invention there is provided an alkylaluminoxane having improved catalytic activity prepared by the process comprising, treating an organic solvent solution of alkylaluminoxane with anhydrous LiX, where X is selected from chloride, fluoride, and bromide.

Also provided is an olefin polymerization catalyst comprising a metallocene and an alkylaluminoxane obtained by treating an organic solvent solution of alkylaluminoxane with anhydrous LiX, wherein X is selected from the group consisting of chloride, fluoride and bromide.

Also provided is an olefin polymerization process comprising contacting an olefin monomer having from 2 to 20 carbon atoms, including mixtures thereof, under polymerization conditions with a catalyst comprising a metallocene and an alkylaluminoxane prepared by treating an organic solvent solution of alkylaluminoxane with anhydrous LiX, wherein X is selected from the group consisting of chloride, fluoride and bromide.

Hydrocarbylaluminoxanes may exist in the form of linear or cyclic polymers with the simplest compounds being a tetraalkylaluminoxane such as tetramethylaluminoxane, $(CH_3)_2AlOAl(CH_3)_2$, or tetraethylaluminoxane, $(C_2H_5)_2AlOAl(C_2H_5)_2$. The compounds preferred for use in olefin polymerization catalysts usually contain about 4 to 20 of the repeating units:

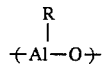

where R is $C_1$-$C_8$ alkyl including mixed alkyl, and especially preferred are compounds where R is methyl. Methylaluminoxanes (MAO's) normally have lower solubility in organic solvents than higher alkylaluminoxanes and the methylaluminoxane solutions tend to be cloudy or gelatinous due to the separation of particles and agglomerates. This problem is frequently encountered with MAOs which have been prepared by adding free water, either neat or contained in a solvent, to a solution of trimethylaluminum as described, for example, in Manyik et al. U.S. Pat. No. 3,300,458. According to such processes, the water-alkylaluminum reaction is carried out in an inert solvent. Any inert solvent can be used. The preferred solvents are aliphatic or aromatic hydrocarbons. Aromatic hydrocarbons are more preferred such as toluene, xylene, ethylbenzene, cumene, mesitylene and the like. The methylaluminoxane products usually contain up to 70% and usually from about 25 to 30 weight percent of unreacted trimethylaluminum.

The invention provides more soluble and more catalytically active alkylaluminoxanes by treating the cloudy or gelatinous MAO solutions, which contain from about 0.5 to 30 weight percent aluminum values, with anhydrous lithium chloride, fluoride or bromide, including mixtures thereof, in proportions of at least about 0.01, and preferably from 0.02 to 0.2, moles of lithium salt per mole of aluminum in the alkylaluminoxane. Larger portions of lithium salt can be used but are not necessary.

The treatment can be accomplished by adding the salt to the alkylaluminoxane solution with stirring for from about 1 to 4 hours at ambient temperatures (15°–30° C.). The time is not particularly critical, and longer or shorter times, which are effective to provide a clear solution can be used. Higher or lower temperatures can also be used.

After the treatment, the solids, including the treating compound, are conveniently removed from the solution by filtration but they can also be removed by any conventional liquid-solid separation techniques such as by settling or centrifugation followed by decanting the liquid.

Because of the increased solubility resulting from the lithium halide treatment, highly concentrated solutions of MAO (up to 50–60 weight percent) in toluene are obtainable via this process. This is an important advantage for storage (reduced capital expenditure on tanks) and overseas shipment or transportation in general.

The soluble alkylaluminoxane and especially MAO products are used in combination with a primary catalyst to form catalyst systems which are useful in the dimerization, oligomerization and polymerization of olefins including both aliphatic olefins such as ethylene, propylene, butenes and the like and aromatic olefins such as styrene, and the like or the reaction of other functional groups such as epoxides. Suitable primary catalysts include but are not limited to metal acetylacetonates, metallocenes including derivatives thereof and the like. Preferred primary catalysts for olefin reactions are metallocenes and in such use the treated MAO affords a significant improvement in catalytic activity.

The primary metallocene catalysts can be $d^0$ organometallic compounds of a transition metal such as titanium, zirconium or hafnium. As used in this application the term "metallocene" includes metal derivatives which contain at least one cyclopentadienyl moiety. The catalyst structure may be described as metallocene (or bent metallocene in the case of bis-cyclopentadienyl compounds) with ancillary anionic ligands or hydrocarbyl groups, such as metallocenes of the formula $Z_t(\eta^5-R'_nH_mC_5)_sMX_{4-s}$, where R' is a carbon or a carbon and heteroatom (N, O, S, P, B, Si and the like) containing $C_1$ to $C_6$ alkyl, $C_3$ to $C_{12}$ cycloalkyl or $C_6$ to $C_{14}$ aryl group. Non-limiting examples of such groups include methyl, ethyl, trimethylsilyl, t-butyl, cyclohexyl, phenyl, 4-methylphenyl, 2,4,6-trimethylphenyl and the like. The R' substituents can be different in type and number on each cyclopentadienyl ring and can form fused cyclic groups attached to the ring. Z is a bridging group between two cyclopentadienyl rings such as silane, phosphine, amine or carbon groups, t is 0 or 1, m and n are integers of 0 to 5, m+n=5 when t is 0 and 4 when t is 1, s is 1 or 2, M is the transition metal and X is halogen, psuedohalogen, (e.g. a leaving group in nucleophilic substitution such as ester, cyanide, tosylate, triflate, β-diketonate and the like), hydride or $C_1$ to $C_8$ alkyl. Analogous metallocenes with two different X groups are also effective in the presence of an aluminoxane. Also effective are bimetallic μ-oxo analogues such as $O[ClHf(C_5H_5)_2]_2$ and mono-cyclopentadienyl metal trihalides.

These and other metallocenes are well known in the art and are described, for example, in published European patent application No. 0 129,368 and U.S. Pat. Nos. 5,017,714, 5,026,798 and 5,036,034, whose teachings with respect to such metallocenes are incorporated herein by reference.

Specific non-limiting examples of metallocenes which are useful in forming the catalysts of the invention include bis(cyclopentadienyl)zirconium dichloride, bis(cyclopentadienyl)hafnium dichloride, bis(pentamethylcyclopentadienyl)hafnium dichloride, bis(indenyl)hafnium dichloride, bis(methylcyclopentadienyl)hafnium dichloride, racemic and meso dimethylsilanyl bridged bis(methylcyclopentadienyl)hafnium dichloride, bis(cyclopentadienyl)titanium dichloride, bis(ethylcyclopentadienyl)zirconium dimethyl, bis(β-phenylpropylcyclopentadienyl)zirconium dimethyl, bis(methylcyclopentadienyl)zirconium dimethyl, racemic dimethylsilanyl bridged bis(indenyl)hafnium dichloride, racemic ethylene bridged bis(indenyl)zirconium dichloride, ($\eta^5$-indenyl)hafnium trichloride and ($\eta^5$-$C_5Me_5$)hafnium trichloride, and the like.

The catalyst components are used in proportions to provide mole ratios of transition metal atom to aluminum atom of from about 0.0002:1 to 0.2:1 and preferably 0.0005:1 to 0.02:1. The catalyst components can be used in solution or deposited on a solid support. The solid support can be any particulate solid, and particularly porous supports such as talc or inorganic oxides, or resinous support material such as polyolefins. Preferably, the support material is an inorganic oxide in finely divided form.

Suitable inorganic oxide support materials which are desirably employed include Group IIA, IIIA, IVA or IVB metal oxides such as silica, alumina, silica-alumina and mixtures thereof. Other inorganic oxides that may be employed either alone or in combination with the silica, alumina or silica-alumina are magnesia, titania, zirconia, and the like. Other suitable support materials are finely divided polyolefins such as finely divided polyethylene.

The catalysts are effective to produce olefin polymers and especially ethylene polymers and ethylene/α-olefin copolymers. Examples of olefins that can be polymerized in the presence of the catalysts of the invention include α-olefins having 2 to 20 carbon atoms such as ethylene, propylene, 1-butene, 1-hexene, 4-methyl-1-pentene, 1-octene, 1-decene, 1-dodecene, 1-tetradecene, 1-hexadecene, and 1-octadecene. Polymerization of ethylene or copolymerization with ethylene and an α-olefin having 3 to 10 carbon atoms is preferable. Such polymerizations may be performed in either the gas or liquid phase (e.g. in a solvent, such as toluene, or in a diluent, such as heptane). The polymerization can be conducted at conventional temperatures (e.g., 0° to 120° C.) and pressures (e.g., ambient to 50 kg/cm$^2$) using conventional procedures as to molecular weight regulation and the like.

The invention is further illustrated by, but is not intended to be limited to, the following examples.

The following examples were carried out under inert atmosphere conditions, using Schlenk glassware and vacuum line, in conjunction with a N$_2$-drybox. Solvents were distilled using standard methods. Filtration and vacuum distillation were done inside a N$_2$-drybox and distillates were collected in a trap at −78° C. Lithium halides were purified by heating in a vacuum oven overnight. Aluminoxanes were obtained from stock solutions produced by Ethyl Corporation.

EXAMPLE 1

A 10 wt % toluene solution of methylaluminoxane (MAO, 270 mmol Al) was placed in a reaction flask, in a N$_2$-drybox. Lithium chloride (LiCl, 13.5 mmol) was added in batches during a period of about 15 minutes. After addition, the mixture was stirred at room temperature for one hour. The mixture was then heated at 70° C. (oil bath) for another two hours. Upon cooling, the mixture was filtered through a medium frit. Filtration was relatively easy. Ordinarily it is very difficult to filter regular MAO through a medium frit. The liquid product was divided into two parts. One part was bottled for storage and the other part was further concentrated. The initial product contained about 96% of the original aluminum value. Both liquid products (12.6 wt % and 28.1 wt % MAO) remained gel free even after 12 weeks. Ordinarily, a 10 wt % solution of MAO in toluene initiates gelation after about one or two weeks. Additionally, the products are found to be about 50% more active than regular MAO when used in conjunction with zirconocene dichloride for ethylene polymerization (Table 3).

EXAMPLE 2

This procedure was performed to investigate the effectiveness of this procedure in large scale reactions. A toluene solution of MAO (870 g, 1479 mmol Al) was placed in a reaction flask. LiCl (3.2 g, 74 mmol) was added in batches. The mixture was stirred at room temperature for two hours followed by heating at 70° C. (oil bath) for another 3 hours. Filtration through a medium frit was relatively easy. Soluble aluminum value recovered was 92% of the original. The product was found to be very active in ethylene polymerization (Table 3).

EXAMPLE 3

Lithium chloride (1.12 g, 26 mmol) was allowed to react with a solution of MAO in toluene (120 g, 252 mmol Al), as described in Example 1, except that the Al/LiCl mole ratio is 10 instead of 20. Analysis showed that 84% of the original aluminum value was recovered. Chloride incorporation into the MAO solution was also negligible. Tables 1 and 2 show product analysis.

EXAMPLE 4

A 30 wt % solution of MAO in toluene (340 mmol Al) was treated with LiCl (2.88 g, 68 mmol) as described in Example 1. Analysis of products is shown in Tables 1 and 2. The product was found to be very active in ethylene polymerization (Table 3). The increase in the amount of LiCl used did not appear to have any adverse affect on the quality of the product.

EXAMPLE 5

This procedure was performed in order to investigate if a smaller amount of LiCl would effectuate clarification and stabilization. A Al/LiCl mole ratio of 0.02 was used. Thus a 10 wt % solution of MAO in toluene (204 mmol Al) was treated with LiCl (4 mmol) as described in Example 1. The product was found to be very stable (Table 2) and active in ethylene polymerization (Table 3). However, filtration was slightly difficult. Therefore, larger amounts of LiCl are recommended for easy filtration.

EXAMPLE 6

All the above described examples used heat. This procedure investigated the effect of the absence of heat in the quality of the product. A solution of MAO in toluene (240 mmol Al) was treated with LiCl (12 mmol). The mixture was stirred at room temperature for 14 hours and then was worked up as described in Example 1. Filtration was difficult, but a clear ("water white") solution was obtained. The product was found to be very active in ethylene polymerization. Thus, heat provides an easily filtrable product but had no apparent effect on the quality of the product.

COMPARATIVE EXAMPLE 1

No lithium chloride was used in this comparison in order to demonstrate the effectiveness of the lithium salt treatment. A 10 wt % solution of MAO (201 mmol Al) was filtered through a medium frit. Filtration was extremely difficult. Only about 62% of the initial aluminum value was recovered in the product. The results as reported in Table 2 shows that the clarity and stability of the untreated products were clearly inferior to those which had been treated with lithium salts. Furthermore, the activity in ethylene polymerization was lower (Table 3).

COMPARATIVE EXAMPLE 2

No lithium salt was used in this comparison but heat was applied in order to demonstrate the effect of heat on the MAO solution. A 10 wt % solution of MAO in toluene (161 mmol Al) was heated at 70° C. (oil bath) for about four hours. The mixture was then worked-up as described in Example 1. Filtration was very difficult. The amount of recovered aluminum value (74%) was improved in comparison with the comparative Example 1. However, Table 2 shows that the stability of the product was inferior to the lithium salt treated MAO solutions.

EXAMPLE 8

A 30 wt % MAO solution in toluene (294 mmol Al) was treated with LiF (58.8 mmol). After stirring at room temperature for one hour, the mixture was heated at 80° C. for 2 hours. A high density lower layer formed. On cooling, this transformed to a cake-like solid layer, which contained most of the aluminum value.

The procedure was repeated without heating. After filtration, only about 56% of the initial aluminum value was recovered as soluble aluminum but the soluble product was found to be extremely active in ethylene polymerization.

EXAMPLE 9

A 10 wt % solution of MAO in toluene (217 mmol Al) was treated with LiBr (10.8 mmol) as described in Example 1. A small amount of thick oily-solid gel appeared at the bottom of the reaction flask. The mixture was first decanted and then filtered. Filtration was very easy. The liquid product contained 76% of the original aluminum value. The product showed superior activity compared to untreated MAO (Table 3).

COMPARATIVE EXAMPLE 3

Clarification of MAO solution in toluene was very effective using LiI. Thus, LiI (1.1 g, 82 mmol) was added to a 10 wt % solution of MAO toluene (163 mmol Al). The reaction was done as described in Example 9. The clear, colorless liquid product was found to be stable even after 12 weeks. However, this material is relatively inactive in ethylene polymerization. It would appear that a small amount of contained iodide interferes with the polymerization mechanism.

TABLE 1

Treatment of Methylaluminoxane (MAO) With Lithium Halides (Product Analysis)

| Example | Reaction[1] Condition | Reagent | Reagent/Al Mole Ratio | Filtration[2] (Med. Frit) | Soluble Al Recovered % | Mole Ratio Al/Cl |
|---|---|---|---|---|---|---|
| Example 1 | A | LiCl | 0.05 | E | 96 | 63 |
| Example 2 | A | LiCl | 0.05 | E | 92 | 114 |
| Example 3 | A | LiCl | 0.10 | E | 84 | 49 |
| Example 4 | A | LiCl | 0.20 | E | 95 | 47 |
| Example 5 | A | LiCl | 0.02 | SD | 93 | 191 |
| Example 6 | B | LiCl | 0.05 | D | 83 | 77 |
| Comp. Ex. 1 | B | — | — | VD | 62 | — |
| Comp. Ex. 2 | A | — | — | VD | 74 | — |
| Example 7 | B | LiF | 0.05 | D | 71 | — |
| Example 8 | B | LiF | 0.20 | NF | 56 | — |
| Example 9 | A | LiBr | 0.05 | E | 76 | — |
| Comp. Ex. 3 | A | LiI | 0.05 | E | 72 | — |

[1]Reaction condition; A = Heat, B = No heat
[2]Filtration; E = Easy, D = Difficult, SD = Slightly difficult, VD = Very difficult, NF = Not filtered but decanted

EXAMPLE 7

A 10 wt % solution of MAO (70 g, 153 mmol Al) was diluted with toluene (100 g). The solution was then treated with LiF (0.2 g, 7.7 mmol). The mixture was stirred at room temperature for 4 hours. The mixture was initially filtered through coarse frit and then through medium frit (slow and difficult filtration). Due to the difficulty in filtration only 71% of the original aluminum value was recovered. The product was found to be active in ethylene polymerization (Table 3).

TABLE 2

Stability of Liquid Products

| Examples | Initial Liquid Product | | | Concentrated Liquid Product | | |
|---|---|---|---|---|---|---|
| | Wt % MAO | TMA Content Mole % | Stability[a] (Weeks) | Wt % MAO | TMA Content[b] Mole % | Stability (Weeks) |
| Example 1 | 12.6 | 21 | >12 | 28.1 | 15.8 | >12 |
| Example 3 | 11.4 | 22 | >12 | 23.1 | 20 | >12 |
| Example 4 | 22.2 | 22 | >12 | 46.7 | 20 | >12 |
| Example 5 | 9.7 | 18 | >12 | 32.1 | 19 | >12 |
| Example 6 | 9.2 | 19 | >12 | 39.6 | 12.4 | >12 |
| Comp. Ex. 1[c] | 10.9 | 25 | <2 | 31.6 | 15 | <1 |
| Comp. Ex. 2[d] | 9.5 | 19 | <4 | 30.2 | 16 | <2 |

[a]Defined as the time required for the appearance of gel or precipitates.
[b]Defined as moles of aluminum as TMA (pyridine titration) with respect to total aluminum content
[c]Regular MAO product subjected to filtration and concentration.
[d]Heated but no LiCl was added.

EXAMPLE 10

Polymerization of Ethylene

The products obtained from the above mentioned examples and comparative examples were used in conjunction with zirconocene dichloride to polymerize ethylene according to the following procedure.

Inside a $N_2$-drybox, an autoclave (600 ml) was charged with toluene (250 ml). A mixture of the treated MAO product (10 mmol Al) and zirconocene dichloride ($6.8 \times 10^{-6}$ mol) in toluene (50 ml) was added. The autoclave was then brought out of the dry box and set up in a hood. After reactor was heated to 80° C., ethylene was introduced at 60 psi during 10 minutes. The reaction was quenched by addition of methanol (300 ml). The polyethylene produced was initially air dried, followed by drying in a vacuum oven without heating. The yield of polyethylene and the activity of the catalyst compositions are reported in Table 3.

What is claimed is:

1. An olefin polymerization catalyst comprising a metallocene and an alkylaluminoxane prepared by the process comprising treating an organic solvent solution of alkylaluminoxane, said alkylaluminoxane having been prepared by adding free water to an organic solvent solution of alkylaluminum, with anhydrous LiX, wherein X is selected from the group consisting of chloride, fluoride and bromide, in proportions of at least about 0.01 mole of LiX per mole of aluminum in the alkylaluminoxane.

2. The catalyst of claim 1 wherein said alkylaluminoxane is methylaluminoxane.

3. The catalyst of claim 1 wherein said solvent is an aromatic hydrocarbon.

4. The catalyst of claim 3 wherein said solvent is toluene.

5. The catalyst of claim 2 wherein said LiX is used in proportions of from about 0.01 to 0.2 moles of LiX per mole of aluminum in the methylaluminoxane.

6. The catalyst of claim 1 wherein the mole ratio of metal atom in said metallocene to aluminum atom in said alkylaluminoxane is from about 0.0002:1 to 0.2:1.

7. The catalyst of claim 1 wherein the mole ratio of metal atom in said metallocene to aluminum atom in said alkylaluminoxane is from about 0.0005:1 to 0.2:1.

TABLE 3

Ethylene Polymerization Lithium Halide Treated Methylaluminoxane (MAO)

| MAO Compositon (10 mmol Al) | Zirconocene Dichloride (moles × $10^{-6}$) | Al/Zr mole ratio | Activity (×$10^6$) g(PE)/mol. Zr · atm · hr | Activity Compared to Untreated MAO | PE (g) |
|---|---|---|---|---|---|
| Example 1 | 6.8 | 1470 | 9.51 | 1.57 | 44 |
| Example 2 | 6.8 | 1470 | 8.87 | 1.46 | 41 |
| Example 4 | 6.8 | 1470 | 8.00 | 1.32 | 37 |
| Example 5 | 6.8 | 1470 | 9.30 | 1.54 | 43 |
| Example 6 | 6.8 | 1470 | 9.51 | 1.57 | 44 |
| Example 7 | 6.8 | 1470 | 8.65 | 1.43 | 40 |
| Example 8 | 6.8 | 1470 | 11.24 | 1.86 | 52 |
| Example 9 | 6.8 | 1470 | 9.30 | 1.54 | 43 |
| Comp. Ex. 1 | 6.8 | 1470 | 6.05 | — | 28 |
| Comp. Ex. 2 | 6.8 | 1470 | 7.35 | 1.21 | 34 |
| Comp. Ex. 3 | 6.8 | 1470 | 1.08 | 0.18 | 5 |
| Comp. Ex. 3 | 6.8 | 1470 | 1.73 | 0.29 | 8 |

* * * * *